(12) United States Patent
Kumar

(10) Patent No.: US 11,877,794 B2
(45) Date of Patent: Jan. 23, 2024

(54) RF ABLATION DEVICE

(71) Applicant: AtriCure, Inc., Mason, OH (US)

(72) Inventor: Ram Kumar, Corcoran, MN (US)

(73) Assignee: AtriCure, Inc., Mason, OH (US)

( * ) Notice: Subject to any disclaimer, the term of this patent is extended or adjusted under 35 U.S.C. 154(b) by 908 days.

(21) Appl. No.: 16/750,988

(22) Filed: Jan. 23, 2020

(65) Prior Publication Data

US 2020/0229868 A1 Jul. 23, 2020

Related U.S. Application Data

(60) Provisional application No. 62/844,532, filed on May 7, 2019, provisional application No. 62/795,906, filed on Jan. 23, 2019.

(51) Int. Cl.
| | |
|---|---|
| *A61B 18/14* | (2006.01) |
| *A61M 25/00* | (2006.01) |
| *A61B 17/00* | (2006.01) |
| *A61B 18/00* | (2006.01) |

(52) U.S. Cl.
CPC ..... *A61B 18/1492* (2013.01); *A61M 25/0071* (2013.01); *A61M 25/0082* (2013.01); *A61B 2017/00566* (2013.01); *A61B 2018/00029* (2013.01); *A61B 2018/00357* (2013.01); *A61B 2018/00363* (2013.01); *A61B 2018/00577* (2013.01); *A61B 2018/00982* (2013.01); *A61B 2018/1467* (2013.01); *A61B 2218/007* (2013.01)

(58) Field of Classification Search
CPC ...... A61B 18/1492; A61B 2017/00566; A61B 2018/00029; A61B 2018/00357; A61B 2018/00363; A61B 2018/00577; A61B 2018/00982; A61B 2018/1467; A61B 2218/007; A61B 5/6834; A61M 25/0071; A61M 25/0082

See application file for complete search history.

(56) References Cited

U.S. PATENT DOCUMENTS

| | | | |
|---|---|---|---|
| 7,803,168 B2 | 9/2010 | Gifford et al. | |
| 8,657,805 B2 | 2/2014 | Peh et al. | |
| 8,709,008 B2 | 4/2014 | Willis et al. | |
| 10,548,611 B2 | 2/2020 | Ibrahim et al. | |
| 2002/0042611 A1* | 4/2002 | Sliwa | A61N 7/02 606/1 |
| 2003/0078575 A1* | 4/2003 | Jahns | A61B 18/1492 606/41 |
| 2006/0235381 A1* | 10/2006 | Whayne | A61B 18/1492 606/49 |

(Continued)

FOREIGN PATENT DOCUMENTS

| | | |
|---|---|---|
| WO | WO 2019/140105 | 7/2019 |
| WO | WO 2020/154509 | 7/2020 |

*Primary Examiner* — Adam Z Minchella
(74) *Attorney, Agent, or Firm* — Levine Bagade Han LLP (57) ABSTRACT

Devices, systems, and methods for therapeutically treating tissue. The devices and methods are suitable for minimally invasive surgery or open surgical procedures. More particularly, methods and devices described herein permit accessing and/or treating areas of tissue with a therapeutic device having a hood member with a plurality of channels located therein for applying a vacuum and cooling the areas of tissue as energy is delivered through electrodes located adjacent to or in the hood member.

18 Claims, 10 Drawing Sheets

(56) References Cited

U.S. PATENT DOCUMENTS

| | | | | |
|---|---|---|---|---|
| 2006/0293646 A1* | 12/2006 | Whayne | ............ | A61B 18/1492 |
| | | | | 606/49 |
| 2007/0250058 A1* | 10/2007 | Whayne | .............. | A61B 18/082 |
| | | | | 606/49 |
| 2011/0230799 A1* | 9/2011 | Christian | .......... | A61B 18/1492 |
| | | | | 601/3 |

\* cited by examiner

RF ABLATION DEVICE

CROSS-REFERENCE TO RELATED APPLICATIONS

The present application is a non-provisional of U.S. Provisional Patent Application No. 62/795,906 filed on Jan. 23, 2019 and a non-provisional of U.S. Provisional Patent Application 62/844,532 filed May 7, 2019, the content of both of which are incorporated herein by reference in their entirety.

FIELD OF THE INVENTION

Devices, systems, and methods for therapeutically treating tissue and are suitable for minimally invasive surgery or open surgical procedures. More particularly, methods and devices described herein permit accessing and/or treating areas of tissue with a therapeutic device having a hood member with a plurality of channels located therein for applying a vacuum and cooling the areas of tissue as energy is delivered through electrodes located adjacent to or in the hood member.

BACKGROUND OF THE INVENTION

Atrial fibrillation (also called AFib or AF) is an irregular heartbeat (arrhythmia) that can lead to blood clots, stroke, heart failure and other heart-related complications. Epicardial RF ablation of atrial tissue for treatment of AF is desirable since an ablation device is positioned exterior to the heart and directs the energy towards the heart tissue and away from the esophagus and other structures. The energy from the ablation device draws current through the target tissue, which causes an ohmic heating of the tissue to create a treatment lesion in the tissue. However, there are anatomical and physiological barriers to heat penetration that a unidirectional epicardial ablation device must overcome. Atrial fibrillation surgery requires creation of an ablation or coagulation lesion in atrial tissue. Typically, a physician creates a lesion using energy (including but not limited to cryogenic, radiofrequency, D.C., microwave, laser, electroporation, high-frequency ultrasound or other thermal modalities) to prevent wavelets or electrical signals/impulses that propagate through the atrial tissue to sustain atrial fibrillation or produce atrial flutter, atrial tachycardia, or another arrythmia.

In conventional devices, as the treatment device delivers energy through the heart tissue to cause a resistive heating of the tissue, blood flow in the heart on the endocardial side of the tissue cools the endocardial surface. This cooling effect on the tissue counteracts the temperature increase in the tissue targeted for treatment. In some cases, the heat sink effect from the blood flow is sufficient to prevent an ablation lesion from passing entirely through the thickness of the tissue, which results in undesirable partial thickness lesions. Since the lesion does not form through the entire thickness of tissue in a partial thickness lesion, electrical current can still pass through the region to cause contraction of the tissue. This renders the treatment less effective or ineffective to treat the arrythmia. The inability to form a "full-thickness" lesions means the region of untreated tissue can still conduct electrical impulses through the tissue, making the procedure less effective in treating the arrythmia.

Cardiac motion (i.e., the beating of the heart) also prevents stable contact between the ablating electrode and the target tissue resulting in poor outcomes since RF ablation requires electrical contact between the electrodes of the ablation device and the targeted region of cardiac tissue. This contact can occur through direct physical contact of the electrodes and tissue or electrical contact through a conductive medium that is present between the electrodes and the tissue.

In addition, parts of the posterior left atrial (LA) wall is often covered with epicardial fat, which typically tends to have higher impedance as compared to myocardial tissue. There is also evidence suggesting that a large part of the LA posterior wall is often fibrosed in patients with persistent and long-standing persistent AF. It is believed that fibrosed tissue has higher impedance compared to normal tissue. The presence of high impedance tissue on the epicardial surface significantly reduce the penetration of current from the RF ablation device through the high impedance region, which makes heating of that tissue difficult.

Existing devices do not often address the issues described herein. For example, conventional devices are often unstable in contacting the tissue due to the beating heart surface which results in sub-optimal performance. Alternatively, or in combination, many conventional devices do not address the cooling effect of blood flow, which can cause partial thickness lesions.

The invention described here improves on current unidirectional ablation devices. However, the aspects described herein can be used other devices as well. The improved methods and devices described herein offer improved access to tissue regions within the body, especially those organs in the thoracic cavity. Variations of these methods and devices described herein improve on the ability to treat atrial fibrillation and ventricular tachycardia ablation and can treat selected tissue regions in a precise manner.

SUMMARY OF THE INVENTION

Variations of the systems, devices and methods described herein provide for improved percutaneous endoscopic ablation procedures by allowing improved access to cardiac tissues within the pericardial sac. Additional variations of devices, systems and methods described herein can be used in areas outside of the cardiac space. Variations of the methods, systems and devices described herein include combinations of features of the various embodiments or combination of the embodiments themselves wherever possible.

The present disclosure includes methods and devices for applying energy from an energy supply into a region of tissue and drawing suction from a vacuum source. For example, one variation of the medical device can include a catheter assembly having a working end; a hood member at the working end and having a top surface and a bottom surface, the hood member having an open face on the bottom surface that exposes a recess within an interior of the hood member, the open face having a perimeter with a first edge and second edge extending lengthwise along a longitudinal axis of the hood member, where at least a portion of the perimeter contacts the region of tissue when the open face is positioned on the region of tissue; a first electrode and a second electrode each positioned respectively along the first edge and the second edge, where the first electrode and second electrode are configured deliver energy from the energy supply to the region of tissue; a plurality of walls extending lengthwise within the interior of the hood member, where the plurality of walls form one or more perfusion channels and one or more vacuum channels within the interior of the hood; where the one or more perfusion channels are in fluid communication with a perfusion lumen located within the hood; where the one or more vacuum channels are in fluid communication with a vacuum lumen located within the hood member; and wherein the device is configured such that, when the open face is positioned on the region of tissue, application of a vacuum from the vacuum source produces a vacuum in the vacuum channel to draw a surface of the region of tissue into the open face and into the recess against the plurality of walls.

In one variation of the medical device the perfusion fluid is fluidly coupled with at least one or more vacuum channels such that continued application of the vacuum, when the surface of the region of tissue is in the recess, causes a perfusion fluid in the perfusion channel to flow in the perfusion channel such that the perfusion fluid cools the surface of the region of tissue.

One or more of the electrodes of the devices described herein can include electrode lumens that extend therethrough. These electrode lumens can be in a fluid path of the perfusion lumen/source. Alternatively, the electrode lumens can be fluidly isolated from the perfusion lumen/source. In additional variations, when the electrode lumens are fluidly coupled to the vacuum channel, application of the vacuum causes the perfusion fluid to flow through the first electrode lumen and the second electrode lumen and into the perfusion lumen.

Another variation of the device includes at least one fluidly isolated vacuum channel such that application of the vacuum causes the tissue to seal against the fluidly isolated vacuum channel without drawing perfusion fluid therethrough.

In one variation, the device is coupled to a pump such that activation of the pump drives a cooling fluid through the first electrode lumen and/or the second electrode lumen.

Variations of the hood can include a recess formed by recessing the plurality of walls within the interior of the hood member. The ends of the walls can form an arcuate or angled profile such that the height of the walls that extend from the hood decrease towards a center of the hood. For instance, the walls located closer to the outer edges of the hood can be longer than the walls located towards a centerline or axis of the hood. This arcuate or angled profile assists in drawing a segment of tissue into the hood upon the application of a vacuum through one or more channels.

Variations of the device include channels that are open (or have an open face) along a length of the hood member. Alternatively, the channels can be enclosed over a full length or partial length of the hood member. For instance, one or more fluid delivery/perfusion channels can be fully enclosed within the interior of the hood member such that this enclosed channel is fluidly coupled with another channel through the use of an open region or plenum in the hood. The plenum can be located in a front or rear of the hood.

The devices described herein can include one or more visualization elements and/or one or more illumination elements. Such features allow a user to visualize the treatment area and/or allow visualization while navigating the device to a desired location. Furthermore, the illumination elements can provide visible light or other electromagnetic energy that allows for tracking/locating of the device. In some variations of the device a visualization element and an illumination element are positioned within a transparent cover on a hood member. The transparent cover can be positioned on any portion of the hood member (e.g., front, rear, top surface, and/or bottom surface).

In another variation the present disclosure includes an energy delivery assembly for use with a catheter body to apply energy from an energy supply into a region of tissue and drawing suction through a vacuum source, the where the assembly comprises: a hood member at the working end and having a top surface and a bottom surface, the hood member having an open face on the bottom surface that exposes a recess within an interior of the hood member, the open face having a perimeter with a first edge and second edge extending lengthwise along a longitudinal axis of the hood member, where at least a portion of the perimeter contacts the region of tissue when the open face is positioned on the region of tissue; a first electrode and a second electrode each positioned respectively along the first edge and the second edge, where the first electrode and second electrode are configured deliver energy from the energy supply to the region of tissue; a plurality of walls extending lengthwise within the interior of the hood member, where the plurality of walls form one or more perfusion channels and one or more vacuum channels within the interior of the hood; where the one or more perfusion channels are in fluid communication with a perfusion lumen located within the hood; where the one or more vacuum channels are in fluid communication with a vacuum lumen located within the hood member; and wherein the device is configured such that, when the open face is positioned on the region of tissue, application of a vacuum from the vacuum source produces a vacuum in the vacuum channel to draw a surface of the region of tissue into the open face and into the recess against the plurality of walls.

The present disclosure also includes methods of applying energy to a region of tissue within a body of a patient. For example, such a method can include positioning a hood member against the region of tissue, wherein the hood member includes an open face on a bottom surface that exposes a recess within an interior of the hood member, the open face having a perimeter with a first electrode along a first edge and a second electrode along a second edge, the hood member further comprising a plurality of walls extending lengthwise within the interior of the hood member to form a plurality of channels; applying a vacuum within a first channel of the plurality of channels such that the region of tissue is drawn into the hood member and forms a seal against the bottom surface of the hood member; delivering a perfusion fluid through a second channel of the plurality of channels such that the perfusion fluid cools the region of tissue; applying energy with the first electrode and the second electrode such that an electrical current flows within the region of tissue between the first electrode and the second electrode; and delivering a cooling fluid within the first electrode and the second electrode.

Another variation of the method includes applying the vacuum within the first channel to cause flow of the perfusion fluid through the second channel after the seal is formed against the bottom surface of the hood member.

In an additional variation, the method includes applying the vacuum within the first channel to cause flow of the perfusion fluid within the first electrode and the second electrode such that the perfusion fluid cools the first electrode and the second electrode.

Variations of the methods and devices include use of a cooling fluid within the electrodes that is electrically non-conductive and where the cooling fluid is fluidly isolated from the perfusion fluid that passes over tissue.

Any of the methods described herein can include visualizing a region of the body of the patient with a visualization element coupled to the hood member and/or illuminating the region of the body of the patient with light or other electromagnetic radiation.

DETAILED DESCRIPTION

Before the inventive methods and devices are described, it is understood that the inventive methods and devices are not limited to particular variations set forth herein since various changes or modifications can be made, and equivalents can be substituted without departing from the spirit and scope of the inventive subject matter. As is apparent to those skilled in the art upon reading this disclosure, each of the individual variations and embodiments described herein has discrete components and features that can be separated from or combined with the features of any of the other several variations without departing from the scope or spirit of the present invention. In addition many modifications can be made to adapt a particular situation, material, composition of matter, process, process act(s) or step(s) to the objective(s), spirit or scope of the present invention. All such modifications are intended to be within the scope of the claims made herein. In addition, combination of aspects of variations, or the combinations of the variations themselves are within the scope of this disclosure.

Methods and devices are disclosed herein for providing access to tissue and/or treating tissue. The devices and methods are suitable for minimally invasive surgery or open surgical procedures. The methods and devices described herein discuss the treatment of cardiac tissue for purposes of illustration. However, the methods and devices can be applied in any application where tissue is treated (e.g., via such modes including heating, cooling, mechanical).

The devices described herein allow for creation of cardiac lesion patterns on cardiac surfaces. However, the methods and techniques are applicable to non-cardiac treatments as well. Variations of the devices, methods and procedures described herein include combinations of features of the various embodiments or combination of the embodiments themselves wherever possible.

Figure 1:
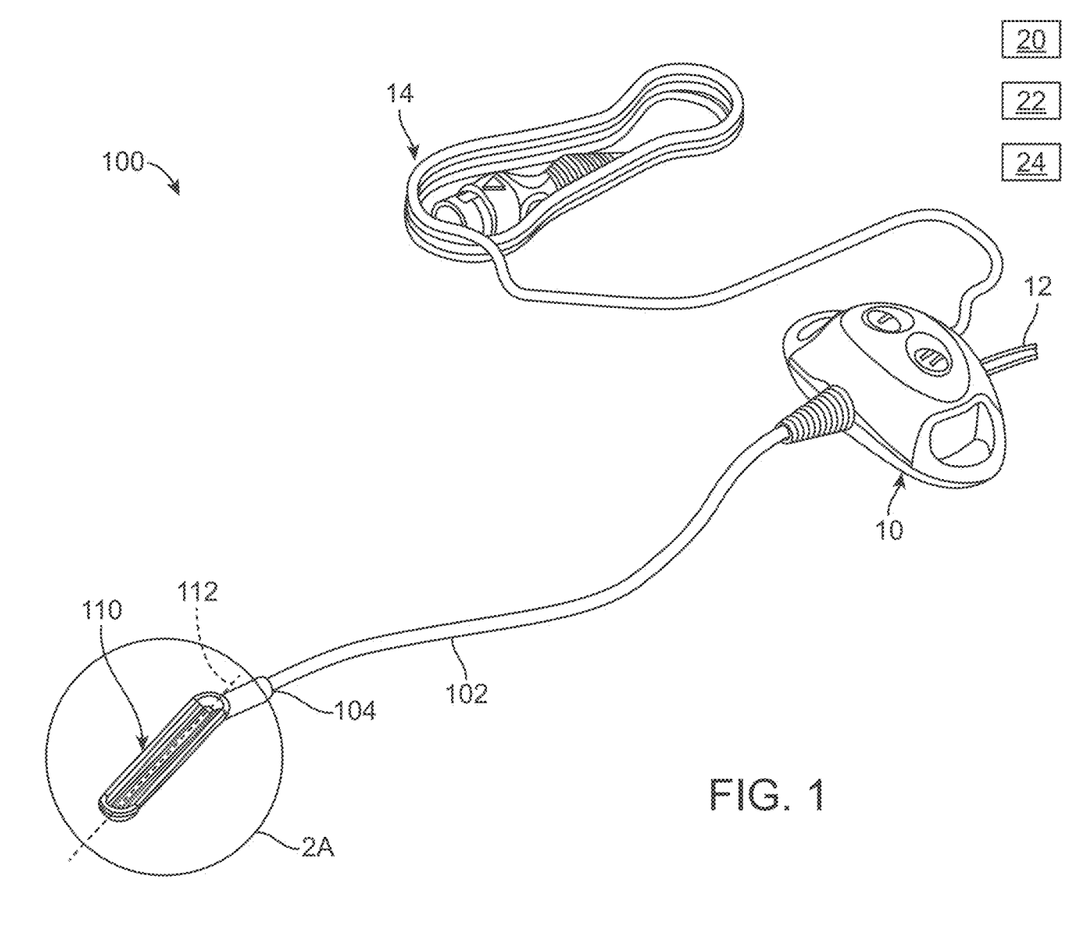
FIG. 1 illustrates an example of a variation of a medical device for applying energy from an energy supply into a region of tissue.

FIG. 1 illustrates an example of a variation of a medical device 100 for applying energy from an energy supply into a region of tissue. As shown, the device 100 includes a hood component 110 that is configured to apply energy to tissue in an improved manner over existing energy delivery devices (including but not limited to RF ablation devices). The hood component 110, as discussed below, includes features that allow for the creation of durable and transmural lesions in cardiac tissue as well as other parts of the body. The variation of the device 100 illustrated in FIG. 1, shows the hood component 110 at a working end 104 of a catheter assembly 102. The catheter assembly 102 can comprise any tube, shaft, or similar component that allows positioning of the hood component 110 as desired. In certain variations, the catheter assembly 102 can comprise a solid shaft component that allows manual positioning of the hood 110. In alternate variations, the catheter assembly 102 comprises a flexible/reinforced/steerable catheter construction that allows for minimally invasive positioning of the hood 110. In yet additional variations, the catheter assembly 102 can comprise a portion of a robotic-assisted system.

FIG. 1 also illustrates the device 100 including an optional base 10 coupled to the catheter assembly 102. The base 10 can provide switches for activating energy delivery and/or fluid delivery, which are both well known by those skilled in the art. Furthermore, the base 10 can include any number of connectors 12, 14 that allow coupling of the device 100 to one or more units 20, 22, 24 that provide energy (e.g., 20), vacuum (e.g., 22), and fluid (24). As is discussed below, the device can include multiple fluid supplies (e.g., for perfusion of tissue and/or cooling components of the device 100). In addition, variations of the device 100 can include one or more footswitches that allow a medical caregiver the option for foot-based activation of the device, which leaves the caregiver's hands-free to position the device or other medical equipment.

As noted above, the hood 110 can be coupled to a distal portion 104 of the catheter body 102. In the illustrated variation, the bottom surface of the hood component 110 is shown facing outwards from the page to better illustrate an open face on the bottom surface that exposes a recess within an interior of the hood (this is further discussed in reference to FIG. 2A below. The hood 110 is also shown to have a longitudinal axis 112 that extends in general alignment with the distal end 104 of the catheter body. However, alternate configurations are within the scope of this disclosure. For example, the working end 104 of the catheter body 102 can be affixed to a medial portion or a side of the hood 110.

Figure 2A:
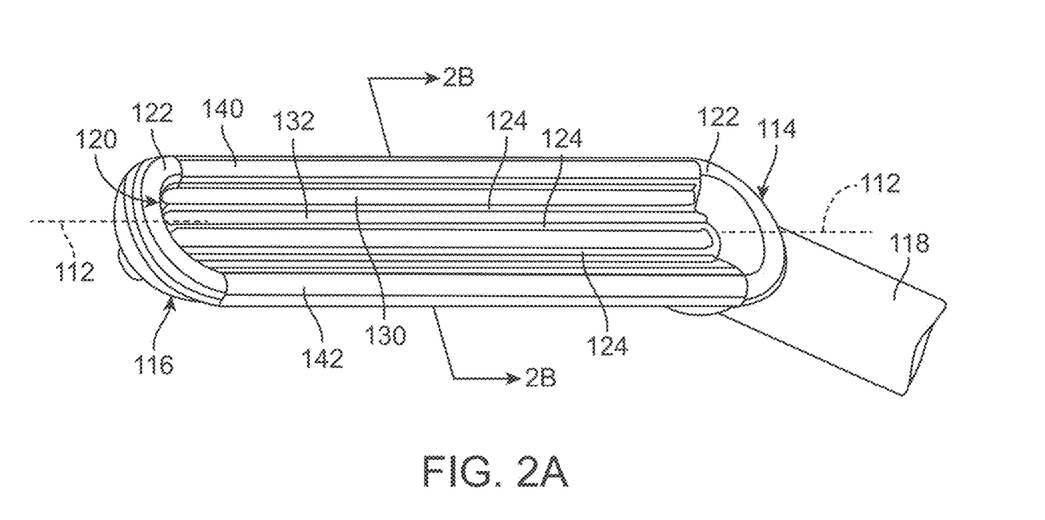
FIG. 2A illustrates a view of the hood component from a bottom surface of the hood component.

FIG. 2A illustrates a view of the hood component 110 from the bottom surface 114. As shown, the hood component 110 includes a longitudinal axis 112 that extends lengthwise along an open face 120 on the bottom surface 114 of the hood 110, which is opposite to an enclosed top surface 116. The open face 120 includes a perimeter or boundary 122 that includes a first and second edge along a length of the hood 110 in general alignment with an axis 112 of the hood 110. As illustrated, a first electrode 140 and a second electrode 142 can be positioned respectively along the first edge and the second edge at the open face 120, where the first electrode and second electrode are configured to couple to the energy supply to deliver energy as discussed below. In certain variations use of the device requires that application of a vacuum through the hood 110 draws a seal against tissue. In such a case, the perimeter or boundary 122 of the open face 120 will be flexible or compressible to conform to tissue. The perimeter region 122 can be planar with an outer edge of the electrodes 140, 142 to improve the ability of the hood 110 to form a seal. In alternate variations, the perimeter region 122 can be offset from the electrodes 140, 142. However, any number of permutations are within the scope of this disclosure. For example, the perimeter regions can be rigid or stiff. In yet additional variations, the perimeter regions 122 can include a passage (not shown) that is in fluid communication with an electrode lumen (discussed below) to allow circulation of a cooling fluid therethrough.

FIG. 2A also shows a plurality of walls or ribs 124 within the hood 110 and extending parallel to the longitudinal axis 112. The plurality of walls 124 forms one or more channels 130, 132 that allow for application of a vacuum to draw tissue within the open face 120 as well as to allow perfusion of the tissue before, after, or during energy delivery. Any number of the channels can be configured to function as perfusion or vacuum channels. Moreover, as discussed below, one or more channels can be configured to draw a vacuum, which allows securing of the hood 110 to tissue, where the vacuum also causes fluid to flow within the channel/hood. In such a case, the channel operates as a vacuum channel and a perfusion channel. The number of walls/ribs 124 illustrated in FIG. 2A is for illustrative purposes only. Variations of the hood component 110 can include any number of walls/ribs necessary to carry out the function of the improved hood 110 as described herein. Furthermore, in another variation, the walls can extend across a length of the hood but at an angle to the longitudinal axis. In yet an additional variation, the walls can extend in a non-linear pattern, such as a serpentine, undulating, zig-zag, or similar pattern as the channels extend across a length of the hood member.

FIG. 2A also illustrates the hood component 110 including a manifold or shaft 118 that allows for coupling of the hood 110 to a catheter member (not shown in FIG. 2A). The manifold/shaft 118 can include any number of lumens or defined openings that function as fluid paths for vacuum, perfusion, and/or cooling. In certain variations of the devices described herein, such fluid paths will be isolated as needed. For example, in variations of the device, it will be desirable to isolate an electrode cooling fluid from a tissue perfusion fluid in those cases where the tissue perfusion fluid is electrolytic (such as a saline solution) and the electrode cooling fluid is electrically non-conductive. In additional variations, a vacuum fluid path will be fluidly coupled to a channel at an end of the channel that is opposite to a perfusion fluid path. This configuration allows for application of a vacuum through the channel, where the vacuum first draws tissue against the open face 120 and subsequently causes the start of perfusion fluid through the channel from the perfusion fluid path. Examples of such configurations are discussed below.

Figure 2B:
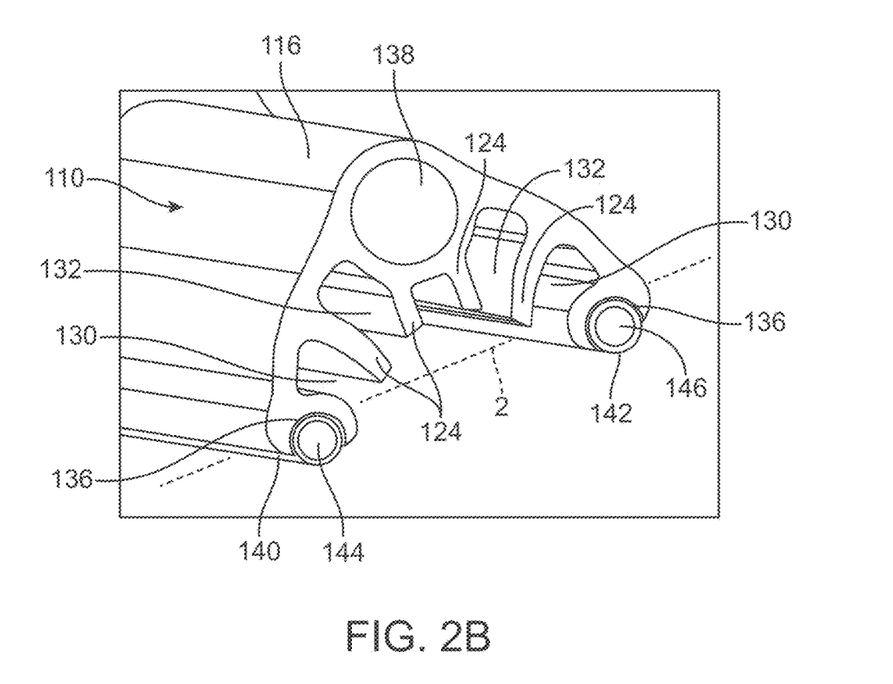
FIG. 2B illustrates a rotated cross-sectional view of the hood member taken along the lines 2B-2B from FIG. 2.

FIG. 2B illustrates a rotated cross-sectional view of the hood member 110 taken along the lines 2B-2B from FIG. 2 to better illustrate the walls 124 forming one or more channels 130, 132 within an interior of the hood 110. The illustration of FIG. 2B shows a bottom surface of the hood 110 and the open face that are placed adjacent to tissue 2. This cross-sectional view shows the plurality of walls 124 forming individual channels 130, 132 that extend along a length of the hood 110. Alternate variations can include channels that extend partially along the hood 110 rather than along an entirety of the hood. Additional variations can include channels that extend at an angle to an axis of the hood.

FIG. 2B also shows a variation of the hood 110 that includes a central lumen 138 that extends through the housing 110. The central lumen 138 can function as a perfusion path or a vacuum path through the hood 110 as discussed herein. The illustration further shows a variation of the hood 110 that includes electrode channels 136 that receive electrodes 140, 142, which further include electrode lumens 144, 146 passing through the electrodes. As discussed herein, certain variations of the device include electrode lumens 144, 146 to provide a flow path of cooling fluid through the electrodes and/or hood.

Figure 3A:
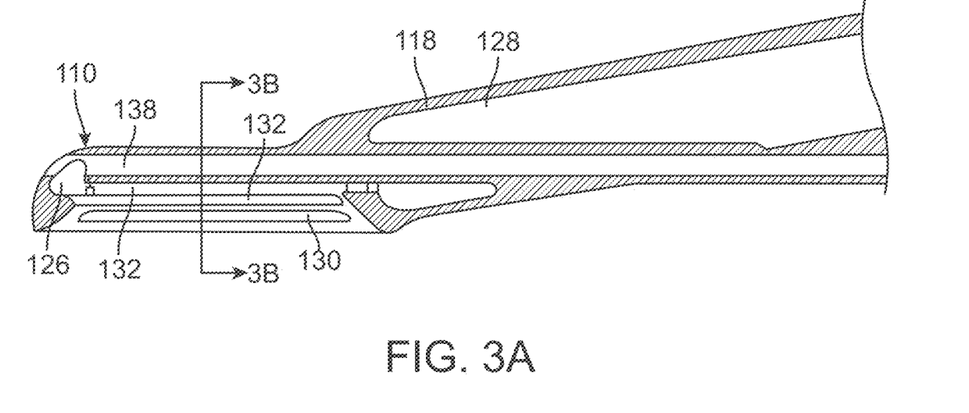
FIG. 3A shows a partial cross-sectional view of a hood member to better illustrate various fluid paths within the hood member.

FIG. 3A shows a partial cross-sectional view of a hood member 110 to better illustrate various fluid paths within the hood member 110. As shown, a central lumen 138 can extend through the hood member 110, where the central fluid lumen 138 is fluidly isolated from other fluid paths (e.g., lumen 128) in a proximal portion of the hood 110. The central lumen 138 can be fluidly coupled to one or more channels 130, 132, using at open region 126 at a distal portion of the hood 110. FIG. 3A also illustrates a manifold 18 or proximal portion of the hood 110 as having a second fluid lumen 128 that is fluidly coupled to one or more channels 130, 132, at a proximal portion of the hood 110. Again, the second fluid lumen 128 will be isolated from the main fluid lumen 138 in the proximal portion of the hood 110. In a variation of the device where the main lumen 138 is coupled to a perfusion fluid source and the second lumen 128 is coupled to a vacuum source, application of a vacuum in the second lumen 128 causes a vacuum to form in the respective channels 132 that are fluidly coupled to the second lumen 128. In the event these channels 132 are fluidly coupled to the main fluid lumen 138 at a distal end of the hood, then formation of a closed fluid system (e.g., by tissue sealing against or within the open face) causes a pressure drop within channels 132. This in turn causes perfusion fluid to flow from the main fluid lumen 138 into the distal portion of the channel 132 and back through the proximal portion and out of the vacuum lumen 128. Clearly, the operation of the device can be reversed such that the main fluid lumen 138 can be coupled to a vacuum source and the second lumen 128 can be coupled to a perfusion source. In such a case, the direction of flow shall be reversed.

In either situation, pulling or pushing perfusion fluid through any channel while other channels form a fluid seal against tissue that causes the perfusion fluid to flow in the channels and cool a surface of the tissue. This is typically desired during energy delivery using the electrodes (not shown in FIG. 3A). As noted above, a number of permutations of perfusion channels and vacuum channels are within the scope of this disclosure. For example, some vacuum channels can be coupled to the vacuum lumen but not the perfusion lumen to allow these channels to produce a seal against the tissue surface and/or some perfusion channels can be coupled to both the perfusion lumen and vacuum lumen to produce a flow of perfusion fluid.

Figure 3B:
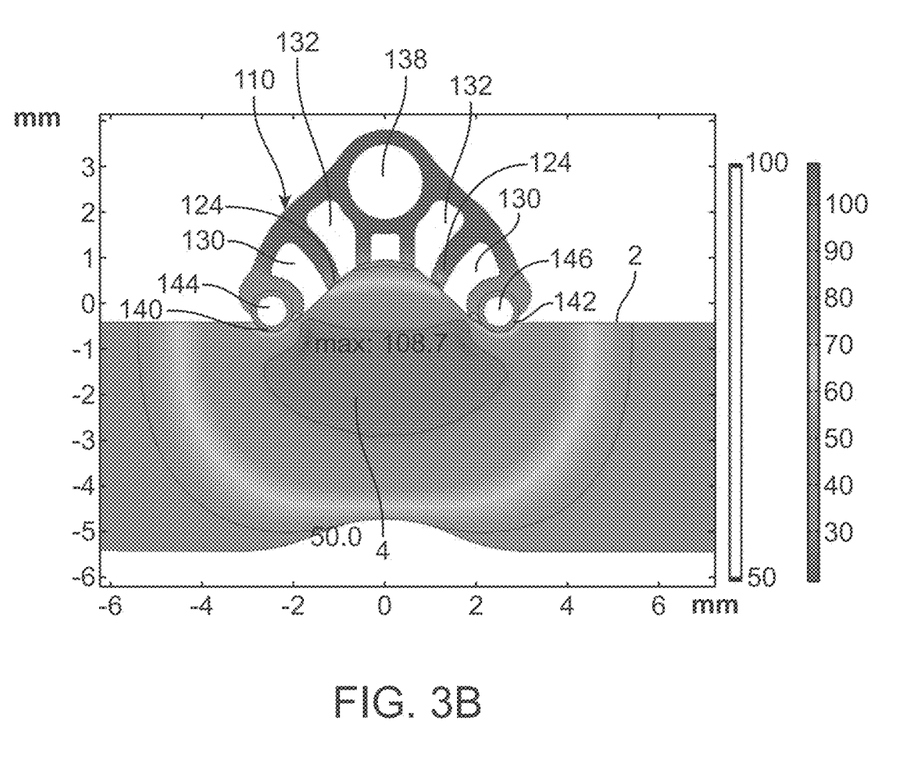
FIG. 3B illustrates a cross-sectional view of a hood member with a vacuum drawn through a number of vacuum channels, which pulls a surface of the tissue within a recess of the hood.

FIG. 3B illustrates a cross-sectional view of a hood member 110 with a vacuum drawn through a number of vacuum channels 132, which pulls a surface of the tissue 2 within a recess of the hood 110. In this variation, the recess within the hood 110 is determined by a distance between the ends of the walls 124 and the open face of the hood as shown in FIG. 2A above. Optionally, the walls 124 of the suction hood 110 form an angle as shown (i.e., the walls closer to a center-line of the hood 110 are shorter than the walls 124 towards the outer edge of the hood 110). Therefore, when the vacuum channels 132 pull tissue towards the walls of the suction hood 110, the tissue forms a tissue recess where the tissue does not fully fold onto itself. This tissue recess reduces the likelihood of trapping blood, which is especially beneficial when used in a cardiac procedure on an endocardial surface of tissue. As noted above, the vacuum channels 132 shown in FIG. 3B can be connected to a vacuum lumen on the proximal side. However, a variety of configurations and shapes of the vacuum lumen may be used.

In addition, one or more perfusion channels 130 can be used to deliver a perfusion fluid over the surface of the tissue 2. This causes a cooling of the surface of the tissue 2. In one variation, where the electrodes are used in a radio frequency mode, current is conducted between electrodes 140 and 142. The tissue heats through ohmic resistance to the current causing an increase in tissue temperature at the area of increased temperature 4. This area of increased temperature 4 creates an ablation or coagulation lesion within the tissue. Meanwhile, delivery of a cooling fluid through electrode lumens 144 and 146 maintains the electrodes at a low temperature to prevent heat build-up at the electrode 140, 142 surfaces. This ensures that the lesion is created within tissue. As noted above, in some cases, failure to maintain an electrode temperature can produce an undesired thermal conductive effect between the electrode surface and the tissue.

As shown in FIG. 3B, the electrodes 140, 142 can be designed with lumens 144, 146 extending therethrough to enable flow of an electrically insulative but thermally conductive fluid, such as but not limited to de-ionized water. This cooling fluid pulls heat away from the electrodes 140, 142. A pump can be used in-line to actively circulate this coolant through the electrode lumens 144, 146. In one embodiment, the flow can be recirculating fluid in a closed-loop system. Alternatively, the fluid may be an open-loop system, which allows for the fluid to start from a large reservoir that empties into the pericardial space. Since the penetration depth for radiofrequency can be minimal and thermal conduction is typically very slow, electrode cooling prevents heat build-up near the electrode and enables ablations for longer durations and more radiofrequency energy input per volume of tissue. In one variation, the flow through the electrodes can be sequential with the coolant entering one electrode on the proximal end and exiting the other electrode on the proximal end. In another embodiment, the coolant flow through the electrode can be parallel resulting in more efficient cooling of the electrode.

An additional feature of the device, shown in FIG. 3B is that once the vacuum pulls tissue into the suction hood 110 causing a seal of the open face of the hood 110 against tissue, the vacuum then also pulls tissue cooling fluid through the fluid inlet and channels. The vacuum pulls tissue cooling flow through the fluid inlet and over the epicardial tissue surface causing cooling of the epicardial surface. The cooling prevents heat accumulation near the electrode and on the epicardial surface and results in more RF energy input per unit volume of tissue. This flow also helps to maintain epicardial tissue temperatures that would otherwise increase the temperature at the top side of the hood 110. The maintenance of temperature at the top of the device opposite to the electrodes can be beneficial from a safety perspective as high temperatures on the device's topside can cause unintended thermal injury to adjacent tissues. For example, failure to maintain such a temperature can produce injury to the esophagus during a cardiac ablation procedure. The esophageal injury can ultimately result in an atrial esophageal fistula, which can be fatal.

FIG. 3B also shows an example of a heat profile during delivery of energy through the electrodes 140, 142. As noted above, the hottest region 4 can ay be 1-2 mm from the epicardial surface (or 1-2 mm closer to the endocardial surface), which may result in deeper penetration of heat. Thus, this region 4 has a higher likelihood of overcoming the endocardial convective effect from blood flow. This can allow creation of full transmural (full-thickness) lesions in cardiac tissue or during other ablation procedures. The primary reasons for the increased depth of penetration of heat in the illustrated variation is due to the slight tissue recess and the effects of electrode and tissue cooling.

Figure 4:
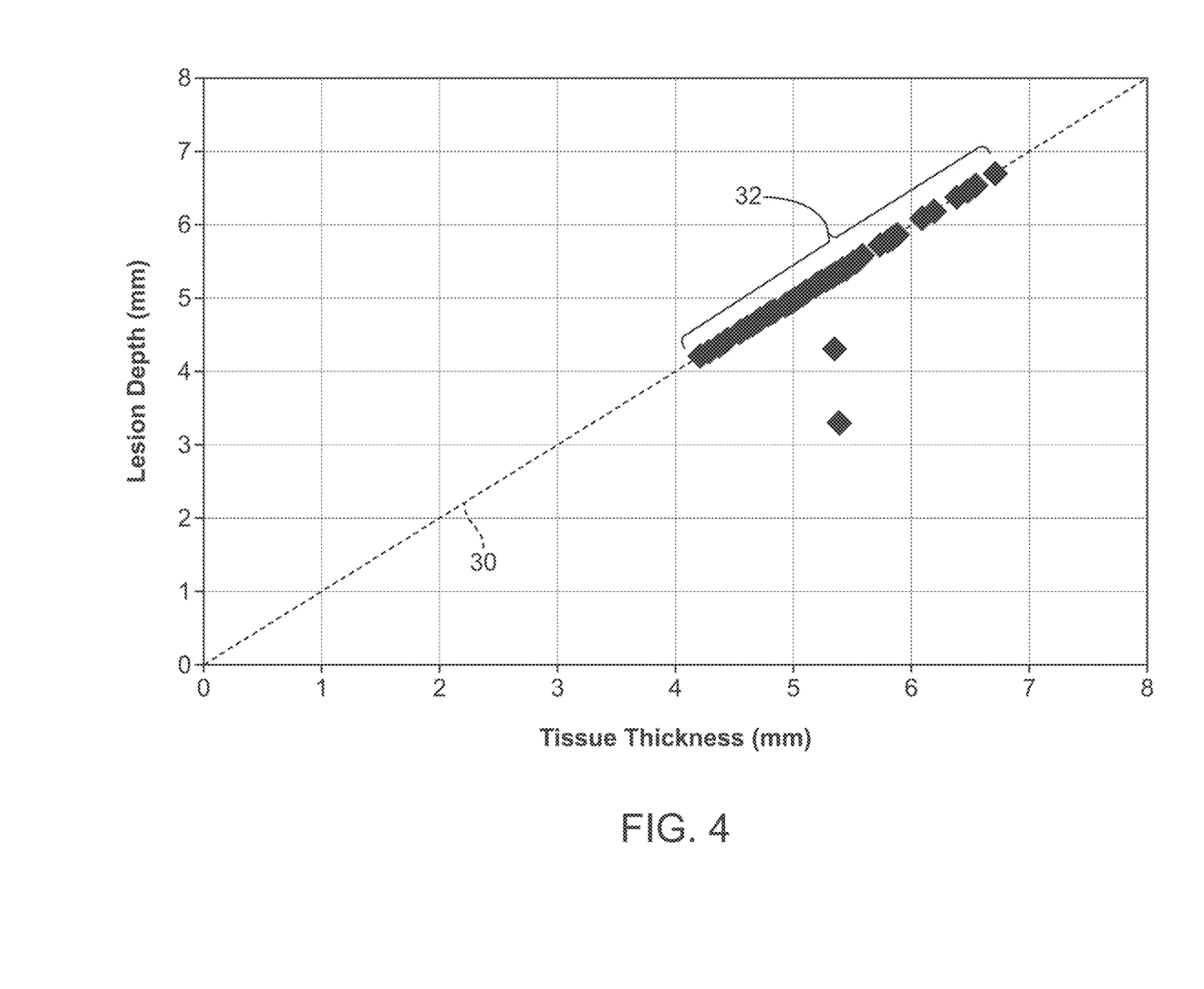
FIG. 4 shows a chart of data from a bench model using the device described herein.

FIG. 4 shows a chart of data from a bench model using the device described herein. The plot shows lesion depth versus tissue thickness with line 30 illustrating the tissue thickness required for a full-thickness ablation lesion. The model used a 5 mm bovine epicardial sample tissue. The resulting lesions are marked at 32, which suggests that more than 95% of the lesion sections were transmural, which compares very favorably to other devices when compared to a similar benchtop configuration.

Figure 5A:
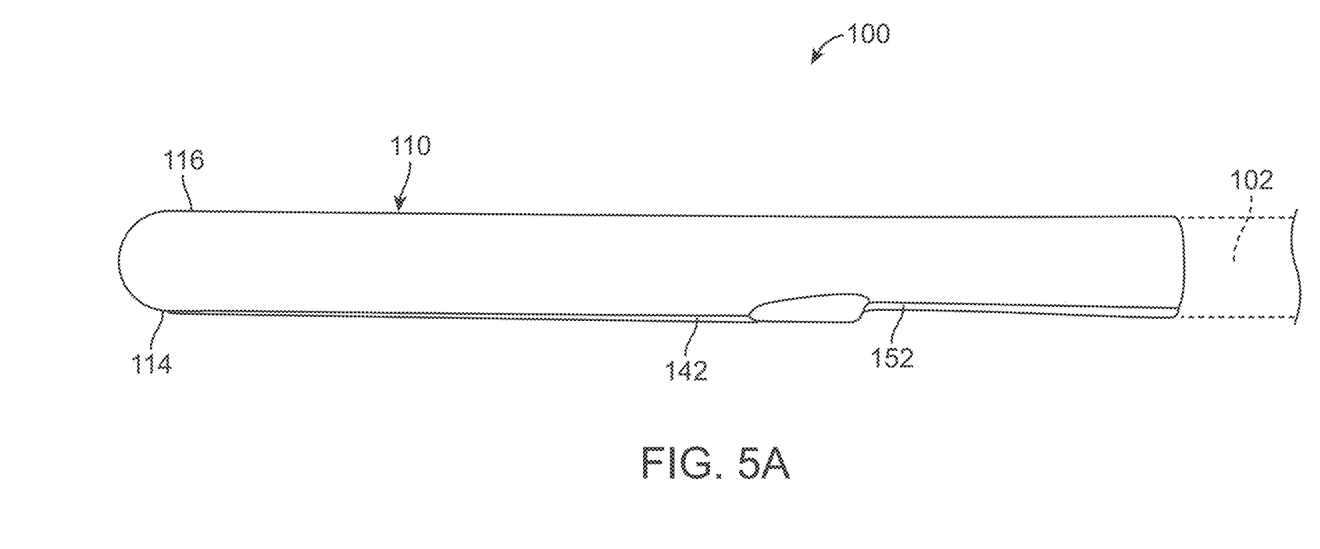
FIG. 5A shows an oblique top view of another variation of a device that is configured to use a cooling fluid that cools both the electrodes as well as the tissue being treated during the procedure.

FIG. 5A shows an oblique top view of another variation of a device 100 that is configured to use a cooling fluid that cools both the electrodes 142 as well as the tissue being treated during the procedure (e.g. epicardial tissue when the device 100 is used for cardiac ablation). In one variation, vacuum lumens and channels are used to form a seal with the tissue and a pump drives any cooling fluid through hollow electrodes. The electrodes can empty the fluid onto the tissue to further cool the tissue. In such a case, vacuum applied through the vacuum lumen and channels enable stable tissue contact between the hood member 110, which pulls tissue into a recess within the hood to create a tissue fold.

It is noted that FIG. 5A illustrates a variation of a hood member 110 comprising an 18 French diameter with an electrode length of 3 centimeters. Clearly, other sizes are within the scope of the disclosure.

In another variation, the vacuum lumens are fluidly coupled to a fluid path of the electrodes so that vacuum pulls cooling fluid through the electrodes to cool the tissue and then over the tissue. In this variation, vacuum acts to pull fluid through the system in addition to secure the hood 110 to tissue. Such a design can allow cooling flow through one or more channels that are near the electrodes only while the remaining channels are primarily used for vacuum to ensure tissue contact. This configuration provides an effective means of cooling tissue near the electrode on the tissue surface.

Turning back to FIG. 5A, the device 100 includes a hood component 110 at a working end of a catheter assembly 102 or shaft, which can contain one or more lumens for supplying fluids and/or vacuum as needed. The hood component 110 includes a pair of electrodes (only electrode 142 is visible in FIG. 5A) that deliver cooling fluid through the electrodes in a distal direction which cools the fluid. The cooling fluid can then exit the electrodes within the hood member 110 such that the cooling fluid flows back over the tissue (and optionally near the electrodes) for an additional cooling effect. As described below, the hood 110 can include additional passages to accommodate a visualizing element, wires, illumination, pacing, sensing, and other structures that aid in the treatment procedure.

Figure 5B:
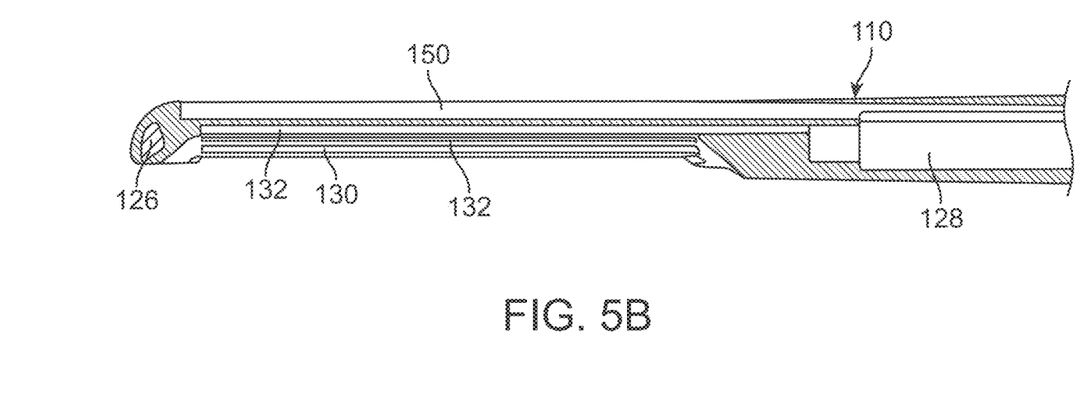
FIG. 5B illustrates a cross-sectional view of the device of FIG. 5A to better illustrate selective use of channels as described herein.

FIG. 5B illustrates a cross-sectional view of the device of FIG. 5A to better illustrate selective use of channels as described herein. FIG. 5B shows a hood member 110 with a number of channels 130, 132 as described herein. The electrodes are not shown in FIG. 5B to better illustrate the flow paths of the channels 130, 132. As noted herein, vacuum can be applied through lumen 128, which pulls a vacuum in all channels 130, 132. However, the channel 130 that is positioned closest to the electrodes is fluidly coupled to a plenum 126, where the plenum 126 is fluidly coupled to lumens of the electrodes. As noted herein, application of a vacuum can draw fluid through the electrode lumens to cool the electrodes, the fluid is then pulled through the plenum 126 and back through the vacuum channel 130 that now functions as a cooling channel 130. The remaining channels 132 are fluidly isolated from the plenum 126, which allows these channels to form a seal against the tissue (as noted with the angled walls described above) to function primarily as vacuum channels 132. FIG. 5B also shows additional passage 150 that can accommodate any number of components, including but not limited to, a visualizing element, wires, illumination, pacing, sensing, and other structures that aid in the treatment procedure.

Figure 5C:
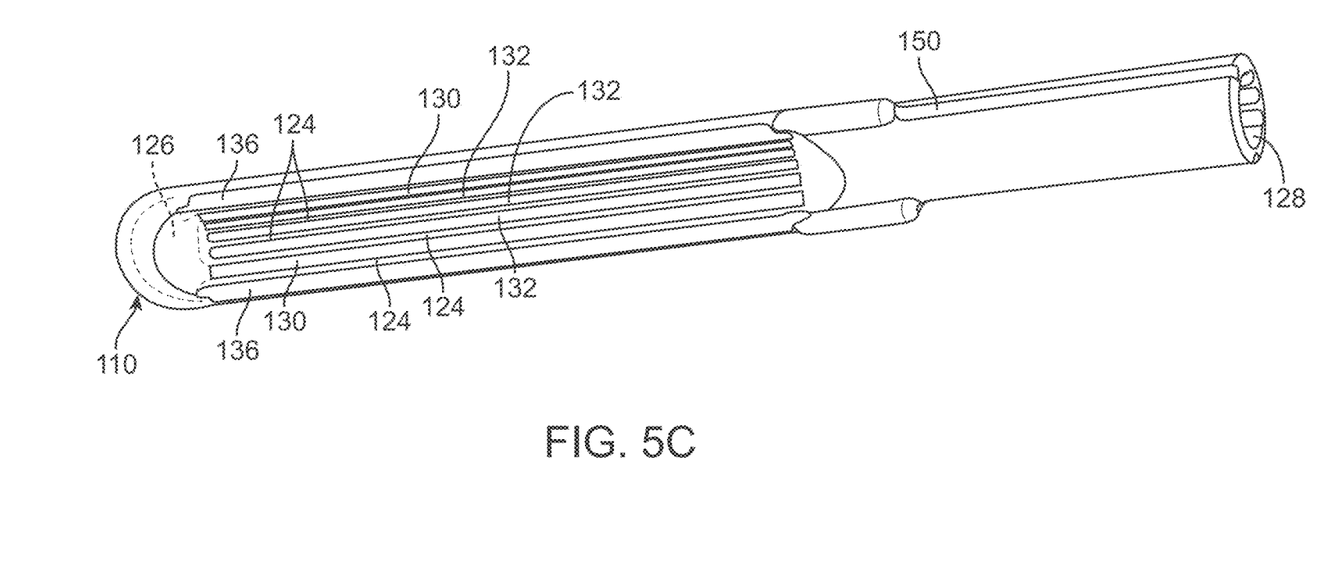
FIG. 5C shows a bottom view of the hood member of FIG. 5A.

FIG. 5C shows a bottom view of the hood member 110 of FIG. 5A to illustrate a plurality of walls 124 extending within a recess of the hood member 110 to form a plurality of channels 130, 132. Again, the hood member 110 is illustrated without the electrodes to demonstrate one variation of a flow path within the hood member 110 and channels 130, 132. As shown, the hood member 110 includes electrode channels 136 that can seat electrodes along lateral edges of the hood 110. The electrode channels 136 are in fluid communication with a plenum 126 located at the distal end of the hood 110. The plenum 126 is also fluidly coupled to a number of channels 130. In this variation the plenum is coupled to the channels 130 adjacent to the electrode channels 136 but any number of configurations is within the scope of this disclosure. In one variation of the device, hollow electrodes are used (as discussed above), where the electrode lumen is in fluid communication with a cooling fluid. The cooling fluid can be pump drive or can be driven using application of a vacuum through channel 128 which forms a vacuum fluid path through the hood 110. When placed against tissue the channels 130 132 pull tissue against walls 124 of the hood 110 to create a seal and secure the hood and electrodes against tissue. In those variations not using a pump, formation of a seal at the channels 130 closes the fluid path between the electrode lumens, which are connected through plenum 126. Therefore, a cooling fluid is pulled through the electrode lumens, through the plenum 126 and through the channels 130 fluidly coupled to the plenum. The fluid is then pulled back through the vacuum path 128. In an alternate variation, in some variations using a pump, the electrodes can deposit fluid directly onto tissue and remains in the body.

Figure 5D:
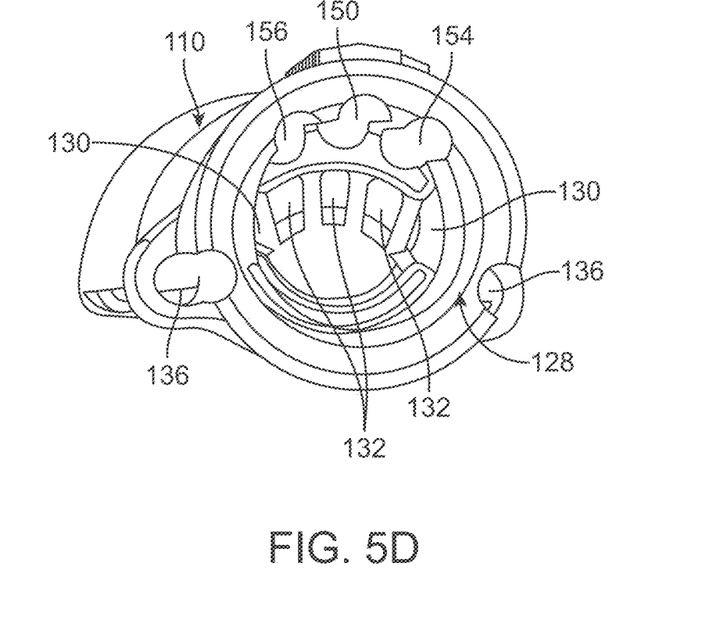
FIG. 5D illustrates a view of the hood member of FIG. 5C, as viewed along the rear and into the vacuum lumen.

FIG. 5D illustrates a view of the hood member 110 of FIG. 5C, as viewed along the rear and into the vacuum lumen 128. As shown, the hood member 110 optionally includes a plurality of lumens 150, 154, 156 used for additional components (e.g., visualization, illumination, sensors, pacing, etc.). The positioning of the lumens allows the components to be passed through the main catheter assembly (not shown in FIG. 5D). FIG. 5D also shows the electrode channels 136 extending along a bottom edge of the hood 110 and the adjacent channels 130 that can be fluidly coupled to the electrode channels 136 as discussed herein.

FIG. 5D also shows the isolated or distally blind vacuum channels 132 that are primarily used to secure tissue to the hood member 110.

Figure 5E:
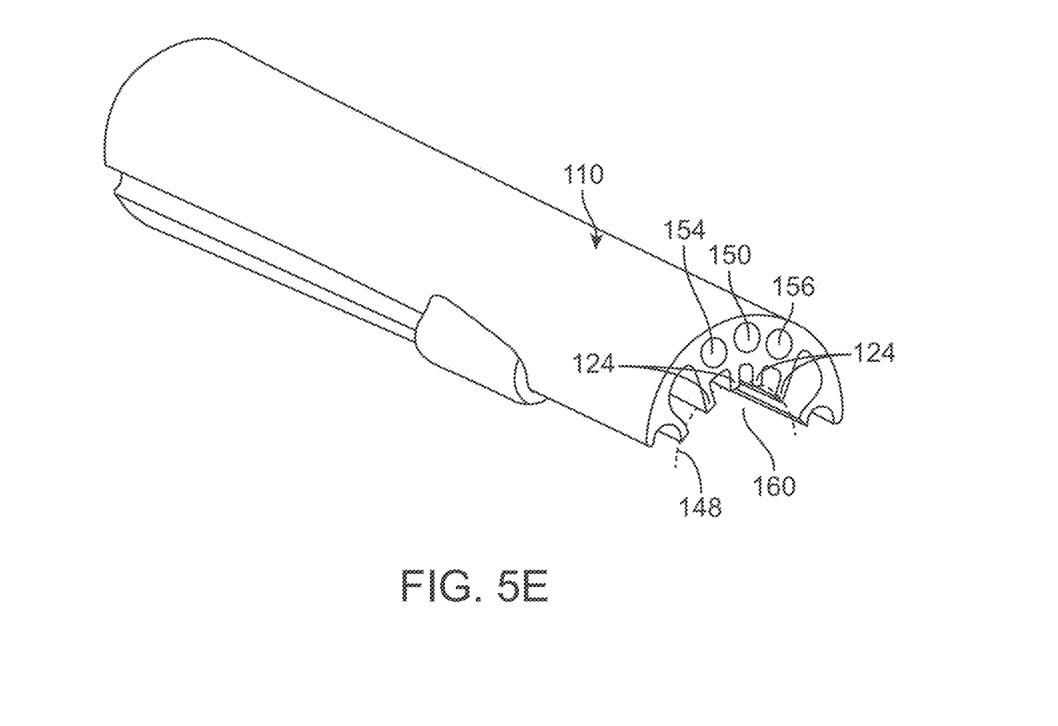
FIG. 5E illustrates partially truncated view of the hood member showing a section through a distal end.

FIG. 5E illustrates a partially truncated view of the hood member 110 showing a section through a distal end. As shown, and as discussed herein, the walls 124 forming channels can be arranged in an angular, tapered, or arcuate profile 148, which allows any tissue that is drawn into the recess 160 within the hood 110 to assume a pre-determined profile that follows the profile 148 of the walls. FIG. 5E also shows the extra passages 150, 154, 156 extending through a distal end, which allows the positioning of illumination and/or a visual element at the distal end of the hood member 110.

Figure 6:
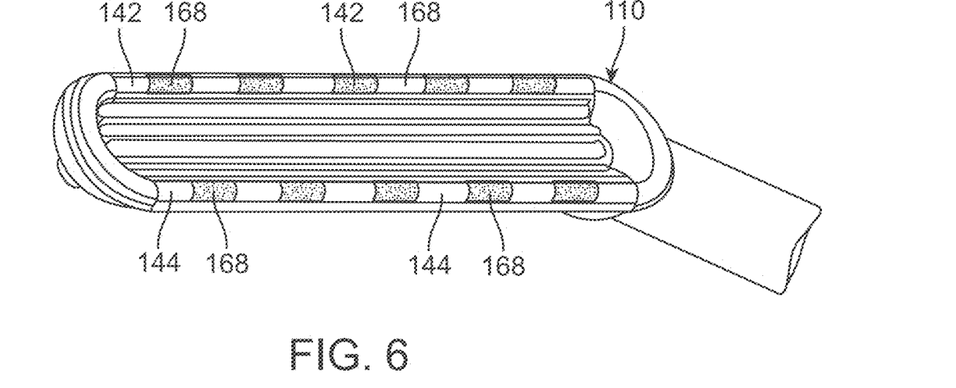
FIG. 6 illustrates a variation of a device having segmented electrodes.

FIG. 6 illustrates a variation of electrodes 142, 144 for use with any variation of the device disclosed herein. The electrodes 142, 144 can be coupled via a connector 168 that can isolate each electrode segment 142, 144 and/or create a flexible electrode that can conform to a flexible hood 110. The segmented electrodes 142, 144 can be paired in any manner desired (e.g., each segment along a specific side can be paired with another segment on that same side, each segment on a specific side can be paired with any other segment on the other respective side, and a combination thereof). Additionally, the electrodes can be used for pacing and sensing or detecting high impedance and potentially preventing higher power delivery.

Figure 7A:
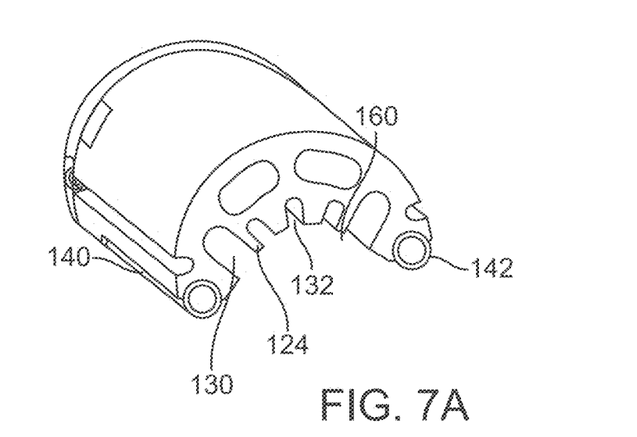
FIGS. 7A and 7B show additional variations of channels within a hood member.
Figure 7B:
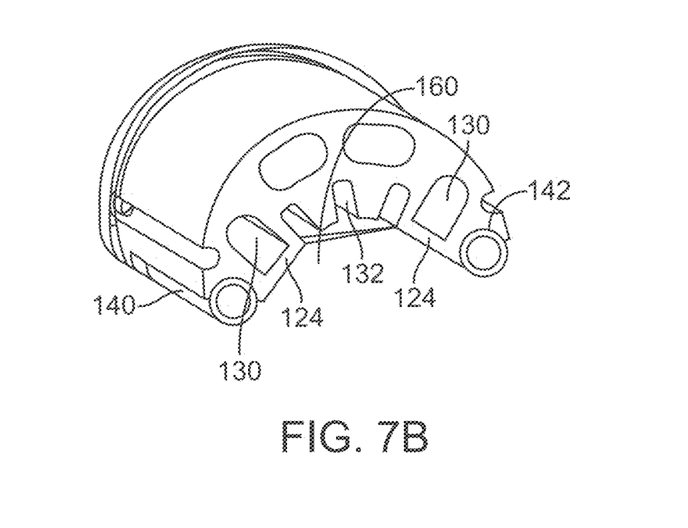

FIGS. 7A and 7B show additional variations of channels 130, 132 within a hood member. In FIG. 7A, walls 124 within the hood member form channels 130, 132 as discussed above, where a portion of the channel remains open to a recess 160 within the hood. Alternatively, as shown in FIG. 7B, one or more channels 130 can be enclosed within the recess 160 to form an enclosed lumen. For example, such an enclosed channel 130 can provide for return-flow of cooling fluid. Alternatively, or in combination, the enclosed channel 130 can serve as a source of cooling fluid that is dispensed at a distal end of the hood (e.g., within a plenum as discussed above.

The devices described herein can benefit from onboard endoscopic visualization to enable physicians to assess the tissue and the device orientation with respect to the tissue prior to ablation. Assessing the device orientation with respect to myocardial tissue can be critical from a safety perspective since ablation with the device oriented away from the myocardium can result in ablation of unintended tissue. Such unintended ablation can present significant adverse effects and can even be fatal. Onboard visualization can also allow differentiation of ablated tissue from unablated tissue, thus helping the physician ablate gaps in the lesion pattern.

Figure 8:
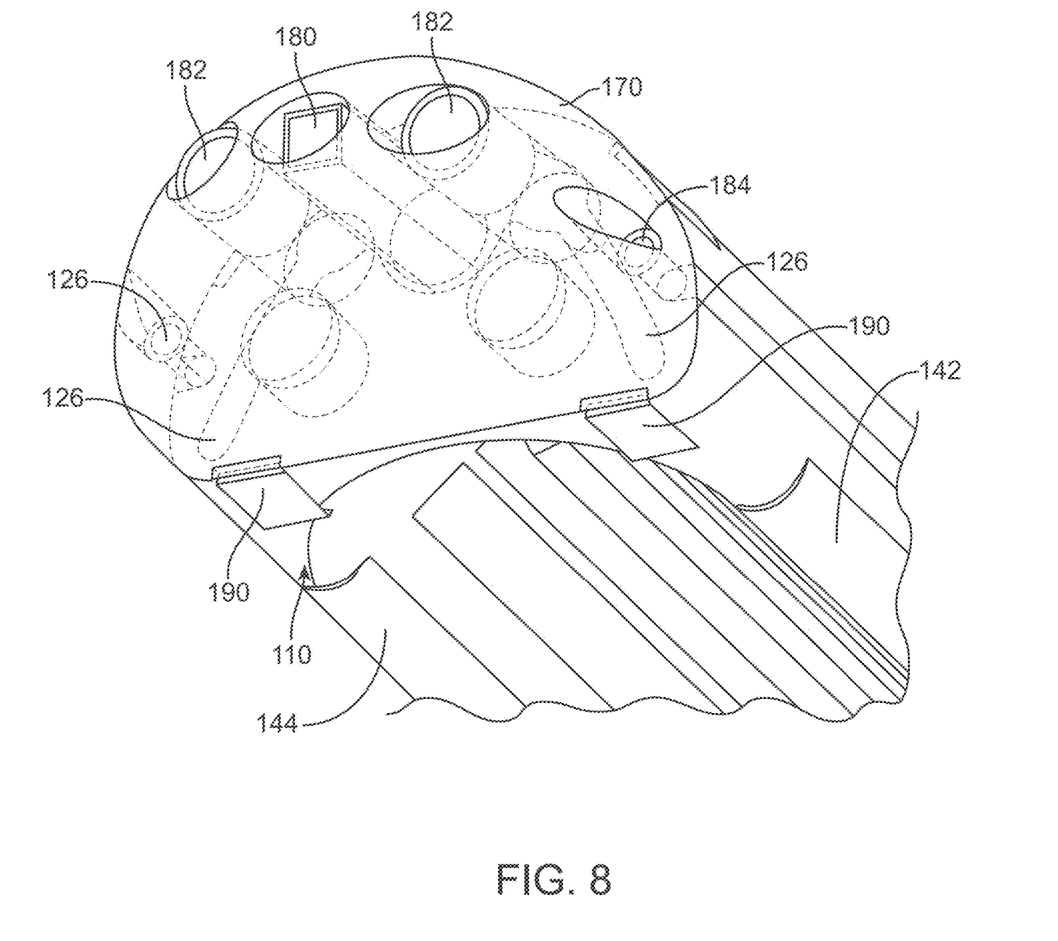
FIG. 8 illustrates visualization and imaging features for use with the devices described herein.

FIG. 8 illustrates yet another feature that can be combined with any variation of the devices described herein. FIG. 8 shows a distal end of a hood member 110 having an imaging sensor 180 (e.g., a CMOS camera, optical fiber, etc.) with one or more illumination sources 182 (e.g., an LED or any illumination source whether visible illumination or non-visible illumination). Such components give the device imaging and illumination ability for observing the lesions and/or positioning of the device. Optionally, the hood member 110 can include a transparent/translucent distal nose tip 170 with the imaging sensor 180 and illumination source 182 placed within the clear tip. This variation was shown to be capable of determining device orientation based on differences in color and contrast between myocardial and pericardial tissue in a pig model-.

The distal tip design can be modular so that it can be mounted on the hood member 110 end-effector. Variations include placement of one or more imaging sensors 180 and/or illumination source 182 on any variety of locations on the hood member 110. For example, the imaging sensor 180 can be placed on an edge of the distal tip 170, which may provide a straightforward perspective. Alternatively, the imaging sensor 180 can be placed along the edge of the distal tip on a slight angle (not shown) to provide a different view of the anatomy. The imaging sensor 180 can be controlled by an image processing box on the proximal end. Additionally, the light source's intensity may also be controlled by the proximal end.

FIG. 8 also illustrates a variation of the hood member 110 having lumens for steering capability. Alternatively, the lumens may provide a means for monitoring temperature of the device as well as providing a conduit for an additional layer of cooling fluid to prevent non-target tissue from ablation. For steering, the lumens can comprise a conduit for anchor pull cables. In addition, the devices described herein can use any navigation sensor 190 that helps position and place the device. Details of such navigation element/sensors 190 are described in PCT/US2019/013074 filed on Jan. 10, 2019 and are incorporated by reference.

Figure 9A:
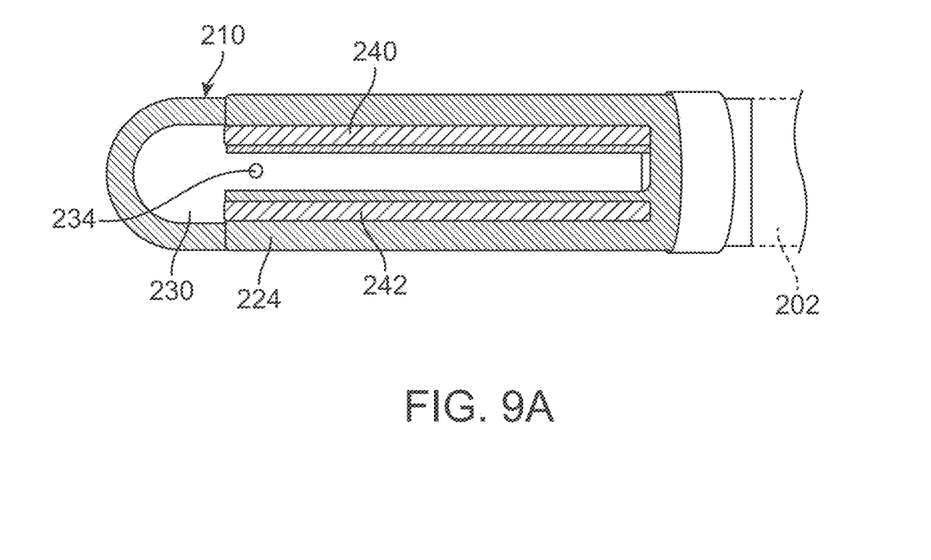
FIGS. 9A and 9B illustrate another variation of a device having a single channel with a pair of electrodes.
Figure 9B:
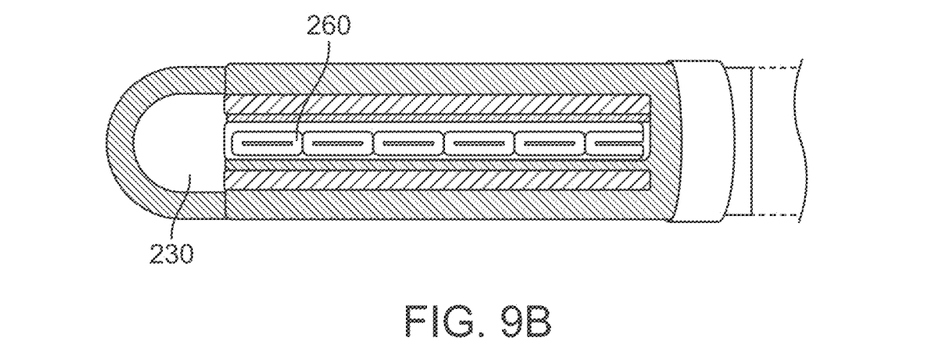

FIGS. 9A and 9B illustrate another variation of a device similar to those described herein. In this variation, a hood 210 includes wall members 224 that define a single channel 230 with electrodes 240, 242 positioned along a side of the interior of the hood 210 within the channel 230. This configuration can be similar to a device manufactured by the Assignee entitled CoolRail® ablation device. In this configuration, cooling flows through the electrodes 240, 242 while the channel 230 provides added vacuum capability and tissue-contacting irrigation. As noted above, there can be separate fluid paths, one for cooling of the electrodes 240, 242 and a port 234 for tissue irrigation. The electrode cooling fluid can optionally remain in a closed system and can be propelled through the device with a pump in the same way as the CoolRail® device. Tissue irrigation can be connected to a separate fluid source and can be driven by a vacuum applied through the catheter assembly or shaft 202 as discussed herein. When suction engages the tissue, irrigation fluid exits the port 234 and the cooling fluid is then be pulled back across the tissue into the main suction lumen. Alternatively, the electrode and tissue can be cooled by the same fluid thus eliminating the need for a separate lumen (e.g., by using electrodes with open lumens).

In any of the disclosed variations, it may be desired to use a suction feature as a retraction accessory to aid completion of lesion sets. In such a case, it can be necessary to prevent fluid from flowing in order to maximize the ability of the vacuum to secure the tissue against the hood member. Therefore, devices described herein can include an on/off (or pause) switch linked to the fluid flow, suction and/or associated controls to prevent ablation without the presence of fluid flow.

Additionally, a tissue recess feature may be desired. An example of a tissue recess feature is shown in FIG. 9B where a plug or similar component 260 is inserted into the vacuum channel 230. Alternate variations can include a mesh, screen, or porous rigid body inserted into the channel.

What is claimed is:

1. A medical device configured to apply energy from an energy supply into a region of tissue and draw suction from a vacuum source, the medical device comprising:
   a catheter assembly having a working end;
   a hood member at the working end and having a top surface and a bottom surface, the hood member having an open face on the bottom surface that exposes a recess within an interior of the hood member, the open face having a perimeter with a first edge and second edge extending lengthwise along a longitudinal axis of the hood member, where at least a portion of the perimeter is configured to contact the region of tissue when the open face is positioned on the region of tissue, the hood member comprising a plenum at a distal end of the hood member;
   a first electrode and a second electrode each positioned respectively along the first edge and the second edge, where the first electrode and second electrode are configured deliver energy from the energy supply to the region of tissue, wherein the first electrode comprises a first electrode lumen extending therethrough and the second electrode comprises a second electrode lumen extending therethrough;
   a plurality of walls extending lengthwise within the interior of the hood member, where the plurality of walls form one or more perfusion channels and one or more vacuum channels within the interior of the hood member;
   where the one or more perfusion channels are in fluid communication with a perfusion lumen located within the hood member;
   where the one or more vacuum channels are in fluid communication with a vacuum lumen located within the hood member;
   where the one or more perfusion channels and the one or more vacuum channels are separated by the plurality of walls, wherein the one or more vacuum channels, the first electrode lumen and the second electrode lumen are fluidly coupled at the plenum;
   where a cooling fluid is introduced through the first electrode lumen and the second electrode lumen, through the plenum, and through the one or more vacuum channels to cool the first electrode and the second electrode; and
   wherein the medical device is configured such that, when the open face is positioned on the region of tissue, application of a vacuum from the vacuum source produces a vacuum in the one or more vacuum channels to draw a surface of the region of tissue into the open face and into the recess against the plurality of walls.

2. The medical device of claim 1, wherein a perfusion fluid is fluidly coupled with at least one or more vacuum channels such that continued application of the vacuum, when the surface of the region of tissue is in the recess, causes the perfusion fluid to flow in the one or more perfusion channels such that the perfusion fluid cools the surface of the region of tissue.

3. The medical device of claim 1, wherein the first electrode lumen and the second electrode lumen are fluidly isolated from the one or more perfusion channels.

4. The medical device of claim 1, further comprising a pump fluidly coupled to the catheter assembly, such that activation of the pump drives the cooling fluid through the first electrode lumen and/or the second electrode lumen.

5. The medical device of claim 4, wherein the first electrode lumen and the second electrode lumen are fluidly coupled with the one or more vacuum channels.

6. The medical device of claim 4, further comprising at least one fluidly isolated vacuum channel such that application of the vacuum draws the tissue against the at least one fluidly isolated vacuum channel without drawing perfusion fluid therethrough.

7. The medical device of claim 1, wherein the first electrode lumen and the second electrode lumen are fluidly coupled to the one or more vacuum channels, such that application of the vacuum causes a perfusion fluid to flow through the first electrode lumen and the second electrode lumen and into the perfusion lumen.

8. The medical device of claim 1, wherein the plurality of walls are recessed within the hood member to form a recess within the interior of the hood member.

9. The medical device of claim 1, wherein a height of the plurality of walls located adjacent to the first edge and second edge is greater than a height of the plurality of walls located adjacent to the longitudinal axis such that an end of the plurality of walls forms an angled profile.

10. The medical device of claim 1, wherein at least one of the one or more vacuum channels is fluidly isolated from the one or more perfusion channels when the region of tissue forms a seal against at least one of the one or more vacuum channels.

11. The medical device of claim 1, wherein at least one of the one or more perfusion channels has an open face within the interior of the hood member.

12. The medical device of claim 1, wherein at least one of the one or more perfusion channels is enclosed within the interior of the hood member.

13. The medical device of claim 1, further comprising a visualization element located on the hood member.

14. The medical device of claim 1, further comprising an illumination element located on the hood member.

15. The medical device of claim 1, further comprising a visualization element and an illumination element positioned within a transparent cover on a distal end of the hood member.

16. The medical device of claim 1, further comprising a navigation element coupled to the hood member.

17. The medical device of claim 1, wherein the first electrode and the second electrode comprise a series of segmented electrodes.

18. An energy delivery assembly for use with a catheter body to apply energy from an energy supply into a region of tissue and drawing suction through a vacuum source, the energy delivery assembly comprising:

a hood member having a top surface and a bottom surface, the hood member having an open face on the bottom surface that exposes a recess within an interior of the hood member, the open face having a perimeter with a first edge and second edge extending lengthwise along a longitudinal axis of the hood member, where at least a portion of the perimeter is configured to contact the region of tissue when the open face is positioned on the region of tissue, the hood member comprising a plenum at a distal end of the hood member;

a first electrode and a second electrode each positioned respectively along the first edge and the second edge, where the first electrode and second electrode are configured deliver energy from the energy supply to the region of tissue, wherein the first electrode comprises a first electrode lumen extending therethrough and the second electrode comprises a second electrode lumen extending therethrough;

a plurality of walls extending lengthwise within the interior of the hood member, where the plurality of walls form one or more perfusion channels and one or more vacuum channels within the interior of the hood member;

where the one or more perfusion channels are in fluid communication with a perfusion lumen located within the hood member;

where the one or more vacuum channels are in fluid communication with a vacuum lumen located within the hood member;

where the one or more perfusion channels and the one or more vacuum channels are separated by the plurality of walls, wherein the one or more vacuum channels, the first electrode lumen and the second electrode lumen are fluidly coupled at the plenum;

where a cooling fluid is introduced through the first electrode lumen and the second electrode lumen, through the plenum, and through the one or more vacuum channels to cool the first electrode and the second electrode; and wherein when the open face is positioned on the region of tissue, application of a vacuum from the vacuum source produces a vacuum in the one or more vacuum channels to draw a surface of the region of tissue into the open face and into the recess against the plurality of walls.

* * * * *